United States Patent
Bossard

(10) Patent No.: US 8,875,559 B2
(45) Date of Patent: Nov. 4, 2014

(54) SYSTEM AND METHOD FOR MEASURING THE CONCENTRATION OF IMPURITIES MIXED WITH HYDROGEN GAS

(75) Inventor: Peter R. Bossard, Ivyland, PA (US)

(73) Assignee: Power & Energy, Inc., Ivyland, PA (US)

( * ) Notice: Subject to any disclaimer, the term of this patent is extended or adjusted under 35 U.S.C. 154(b) by 319 days.

(21) Appl. No.: 13/314,175

(22) Filed: Dec. 7, 2011

(65) Prior Publication Data

US 2013/0145823 A1 Jun. 13, 2013

(51) Int. Cl.
*G01N 7/10* (2006.01)
*G01N 33/00* (2006.01)

(52) U.S. Cl.
CPC .............. *G01N 7/10* (2013.01); *G01N 33/0014* (2013.01)
USPC ............................. 73/31.03; 95/55; 73/31.07

(58) Field of Classification Search
CPC ... G01N 7/10; G01N 33/0014; G01N 33/005; G01N 33/0059; G01N 1/4005; C01B 3/503
USPC ....................... 73/31.07, 31.03; 95/45, 55, 56
See application file for complete search history.

(56) References Cited

U.S. PATENT DOCUMENTS

| | | | | |
|---|---|---|---|---|
| 2,671,337 A * | 3/1954 | Hulsberg | ..................... | 73/31.04 |
| 3,258,896 A * | 7/1966 | Muller | ................................ | 95/8 |
| 3,589,171 A * | 6/1971 | Haley | ............................ | 73/23.37 |
| 3,718,434 A * | 2/1973 | Pierce | ............................ | 436/127 |
| 3,769,837 A * | 11/1973 | Kraus et al. | .................... | 73/31.07 |
| 3,780,496 A * | 12/1973 | Ward et al. | ......................... | 95/53 |
| 4,598,576 A * | 7/1986 | Goldsmith et al. | .......... | 73/31.07 |
| 4,858,461 A * | 8/1989 | Steinle et al. | ................. | 73/31.04 |
| 5,360,467 A | 11/1994 | Katkar et al. | | |
| 7,396,385 B1 | 7/2008 | Bossard et al. | | |
| 2012/0192712 A1 * | 8/2012 | Kurokawa et al. | ................. | 95/19 |

* cited by examiner

*Primary Examiner* — Lisa Caputo
*Assistant Examiner* — Punam Roy
(74) *Attorney, Agent, or Firm* — LaMorte & Associates, P.C.

(57) ABSTRACT

A system and method for taking a sample of hydrogen gas and conditioning that sample so that extremely low levels of contamination can be more accurately detected. Initially a sample of hydrogen gas is captured and isolated in a collection chamber. A hydrogen permeable membrane is provided having a first side and a second side. The first side of the hydrogen permeable membrane is exposed to the gas sample held within the collection chamber. The hydrogen gas contained within the gas sample begins to permeate through the hydrogen permeable membrane and exit the collection chamber. This causes the pressure of the gas sample within the collection chamber to decrease. Since contaminants remain in the collection chamber, the concentration of contaminants within the remaining sample increases exponentially. The residual pressure within the collection chamber is measured and converted into a contaminant level reading.

13 Claims, 1 Drawing Sheet

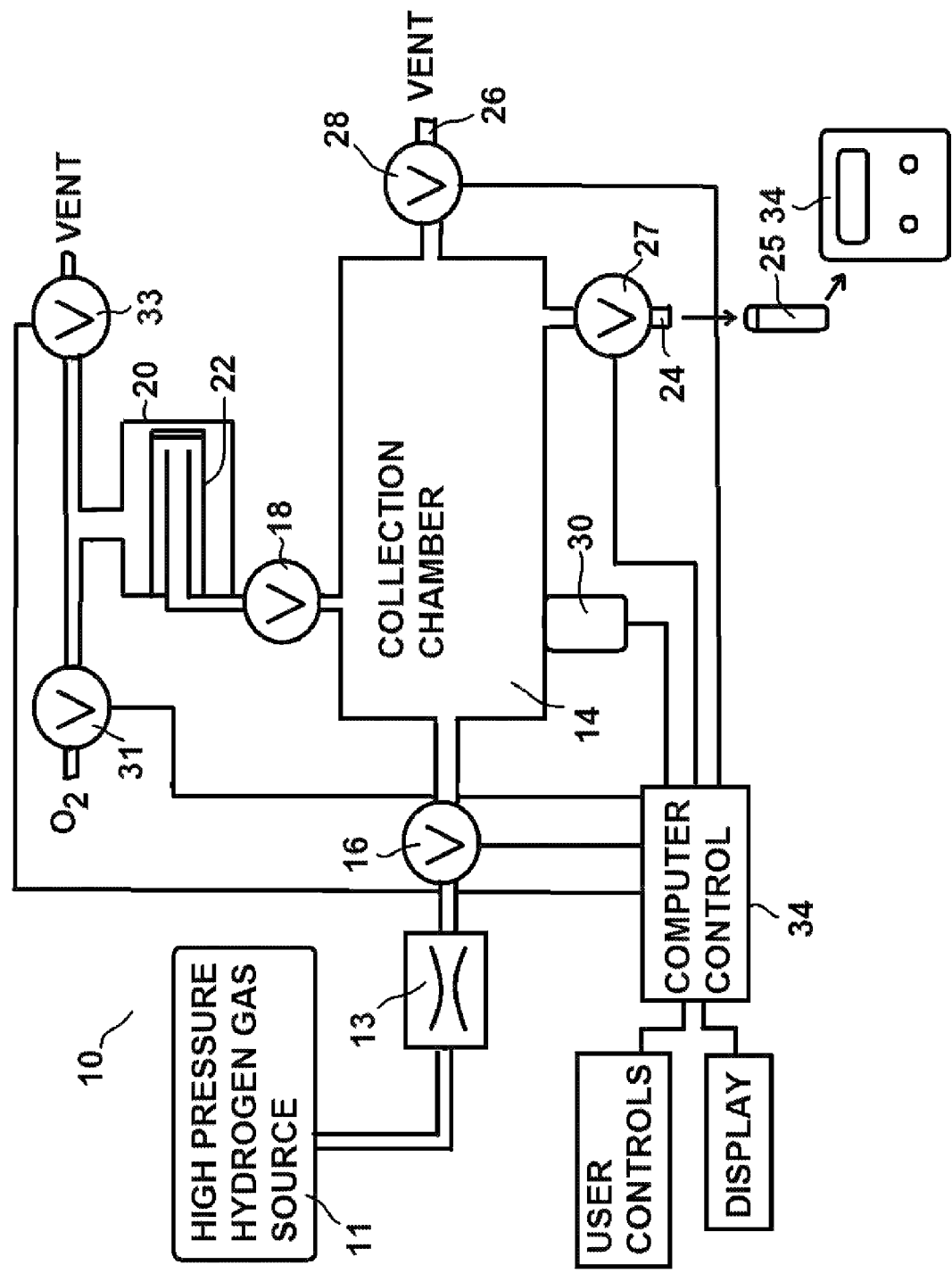

SYSTEM AND METHOD FOR MEASURING THE CONCENTRATION OF IMPURITIES MIXED WITH HYDROGEN GAS

BACKGROUND OF THE INVENTION

1. Field Of The Invention

The present invention relates to systems and methods that sample a volume of hydrogen gas and detect the concentration of impurities in that sample.

2. Prior Art Description

In industry, there are many applications for the use of ultra pure molecular hydrogen. For instance, there are many fuel cells that operate using hydrogen. The hydrogen, however, must be ultra pure. Any molecules of carbon dioxide, carbon monoxide or hydrocarbon gases that are received by the fuel cell cause damage to the fuel cell and decrease both the efficiency and the functional life of the fuel cell.

Ultra pure hydrogen is also used in the manufacture of electronic microprocessors. If the hydrogen gas is contaminated even with a small amount of a contaminant, such as water vapor, the operational integrity of the microchip can be damaged.

Traditionally, ultra pure hydrogen gas is generated using a two-stage process. In the first stage, hydrogen gas is separated from a source gas. For example, hydrogen can be separated from a hydrocarbon gas or can be obtained from water by hydrolysis. However, in many common processes that produce hydrogen, the hydrogen gas produced is not pure. Rather, when hydrogen is produced, the resultant gas is often contaminated with hydrocarbons, water vapor and/or other contaminants. It is for this reason that a second processing stage is used.

In the second processing stage, the separated hydrogen gas is then purified to remove lingering contaminants. In the art, ultra pure hydrogen is commonly considered to be hydrogen having purity levels of at least 99.999%. In the prior art, one of the most common ways to purify contaminated hydrogen gas is to pass the gas through a membrane made of a hydrogen permeable material, such as palladium or a palladium alloy. As the contaminated hydrogen gas passes through the membrane, atomic hydrogen permeates through the membrane, thereby separating from the contaminants. In such prior art processes, a pressure differential is maintained across the membrane. The membrane is typically heated to at least three hundred degrees centigrade. At the membrane, molecular hydrogen disassociates into atomic hydrogen on the surface of the membrane and the membrane absorbs the atomic hydrogen. The atomic hydrogen permeates through the membrane from a high pressure side of the membrane to a low pressure side of the membrane. Once at the low pressure side of the membrane, the atomic hydrogen recombines to form molecular hydrogen. The molecular hydrogen that passes through the membrane can then be collected for use.

In a more modern hydrogen generating technique, hydrogen gas can be generated and separated from a hydrocarbon/water mixture on-demand in a single step process. In a single step process, hydrogen gas is separated from a source gas and purified in a single processing cell. Such a single step generation technique is exemplified in U.S. Pat. No. 7,396,385 to Bossard et al., entitled System And Method For Efficiently Separating Hydrogen Gas From A Mixed Gas Source. However, single stage ultrapure hydrogen generators still rely upon the use of a hydrogen permeable membrane to separate ultrapure hydrogen from contaminants.

The problem is that the hydrogen permeable membranes used in both the dual step and single step hydrogen generating systems do not last indefinitely. The hydrogen permeable membranes are subject to repeated pressure and temperature cycles. Eventually, the hydrogen permeable membranes fatigue and crack. Once cracked, contaminants can pass through the hydrogen permeable membrane with the hydrogen. The collected gas, therefore, is no longer ultrapure.

If a manufacturer does not continuously monitor the purity of the ultra pure hydrogen being used, a contaminant leak could destroy fuel cells, ruin microcircuit production, or otherwise cause harm to a product or manufacturing process. In order to prevent such damage from occurring, many manufacturers periodically test the level of contaminants contained within the ultrapure hydrogen and apply statistical process controls to the collected data to predict when a hydrogen purifier needs to be replaced. In order for statistical process controls to be effectively used, very small increases in contaminants need to be detected and tracked.

In the prior art, ultrapure hydrogen is tested for purity using a mass spectrometer. In order to use a mass spectrometer, a sample of the hydrogen gas is taken. The pressure of the sample is then reduced to under 10 millitorr before it is introduced into a mass spectrometer for analysis. In order to lower the pressure of the hydrogen sample to the required pressure, the sample size is reduced in proportion to its container. This is done by either pumping some of the sample out of its container or introducing the sample into a very large vacuum chamber. In either scenario, the amount of contaminant per unit volume of the sample is reduced in direct proportion to the reduction in pressure. By the time the sample is ready for analysis, the amount of contaminants may be reduced so far that small changes in the amount of contaminants may not be detected.

Contaminants can be concentrated by removing some of the hydrogen in a collected sample using a hydrogen permeable membrane. Such a system is exemplified in U.S. Pat. No 5,360,467 to Katkar. However, the concentrated sample must then be analyzed using a mass spectrometer. Mass spectrometers are very complex and expensive pieces of equipment that are typically only used in research laboratories of companies and hospitals. However, with the increasing popularity of fuel cell technology, many small companies now have the need to test for contaminants in hydrogen gas. For example, some gas stations now provide hydrogen gas as fuel for fuel cell powered cars. By regulation, the hydrogen gas must be periodically tested for purity. Such testing must be outsourced to labs because the gas station does not have a mass spectrometer or the skilled personnel to operate a mass spectrometer. Lab results take time to receive. Accordingly, a gas station may be selling contaminated gas for days before the problem can be detected.

A long standing need therefore exists for a system that can sample hydrogen gas for contamination levels in a simple and inexpensive manner. This need is met by the present invention as described and claimed below.

SUMMARY OF THE INVENTION

The present invention is a system and method for taking a sample of hydrogen gas and conditioning that sample so that extremely low levels of contamination can be more accurately detected. Initially a known volume of supposedly pure hydrogen gas is introduced into a collection chamber. However, the gas being sampled inevitably contains hydrogen gas mixed with trace amounts of contaminant gases. The collection chamber has a much smaller volume than the volume of gas sample being tested.

A hydrogen permeable membrane is provided having a first side and a second side. The first side of the hydrogen permeable membrane is exposed to the gas sample within the collection chamber. The hydrogen gas contained within the gas sample begins to permeate through the hydrogen permeable membrane and exit the collection chamber. This causes the partial pressure of hydrogen gas within the collection chamber to decrease, while the partial pressure of the remaining contaminant gases increases. Since the contaminants remain in the collection chamber, the concentration of contaminants within the remaining sample increases exponentially. Hydrogen gas is drawn out of the collection chamber until the pressure within the collection chamber reaches an equilibrium. At this pressure, the contents of the collection chamber are proportional to the volume of contaminant gases contained within the starting sample. Since the contaminants have been concentrated, very small levels of contaminants can be readily detected merely by measuring the pressure of the gas remaining in the collection chamber.

To further reduce the partial pressure of hydrogen within the collection chamber, hydrogen gas is actively drawn out of the collection chamber. To actively draw hydrogen gas away from the collection chamber, the second side of the hydrogen permeable membrane is exposed to air or another gas that contains oxygen. The hydrogen gas permeating through the hydrogen permeable membrane immediately reacts with oxygen to form water. Accordingly, hydrogen gas is actively drawn away from the hydrogen permeable membrane, and thus the interior of the collection chamber.

BRIEF DESCRIPTION OF THE DRAWINGS

For a better understanding of the present invention, reference is made to the following description of an exemplary embodiment thereof, considered in conjunction with the accompanying drawings, in which:

FIG. 1 is a block diagram schematic of an exemplary embodiment of a collection system in accordance with the present invention.

DETAILED DESCRIPTION OF THE DRAWINGS

Referring to FIG. 1, a schematic of a collection system 10 is illustrated. The collection system 10 takes a sample of hydrogen gas from a high pressure hydrogen gas source 11, such as a hydrogen gas storage tank at a gas station. The sample taken is at a lower pressure than that of the high pressure hydrogen gas source 11. This is achieved using a low pressure tap, a gas restrictor or similar pressure reducing device 13. The pressure of the gas to be samples is preferably reduced to approximately 760 Torr, i.e. one atmosphere.

The collection system 10 contains a collection chamber 14. The collection chamber 14 receives the reduced pressure sample gas. The collection container can have any volume. However, as will be explained, the collection chamber 14 has a volumetric capacity that is at least 100 times less than the volume of the gas sample being tested, with a preferred volumetric capacity of at least 500 times less. For the purposes of explanation, the collection chamber 14 should be considered as having a volume of approximately twenty cubic centimeters. The collection chamber 14 can be isolated using various valves 16, 18, 24, 27.

The first valve 16 is used to control the flow of reduced pressure hydrogen gas into the collection chamber 14. When the first valve 16 is open, the reduced pressure hydrogen gas flows into the collection chamber 14. As will later be explained, the volume of the hydrogen gas sample that passes into the collection chamber 14 is between 100 times and 1000 times the volume of the collection chamber 14, with the preferred volume being approximately 500 times the volume of the collection chamber 14. Accordingly, if the collection chamber has a volume of twenty cubic centimeters, the gas sample that flows through the first valve 16 is preferably ten thousand cubic centimeters.

A hydrogen separator 20 is coupled to the collection chamber 14. The hydrogen separator 20 can be selectively isolated from the collection chamber 14 by a second valve 18. The hydrogen separator 20 contains at least one hydrogen permeable membrane 22. The far side of the hydrogen permeable membrane 22 is exposed to a gas source containing free oxygen, such as bottled oxygen or ambient air. In this manner, any hydrogen molecules that may permeate through the hydrogen permeable membrane 22 in the hydrogen separator 20 will quickly react with the oxygen.

The collection chamber 14 is also coupled to a vent port 26 for purging the contents of the collection chamber 14. A third valve 28 is provided to selectively open and close the vent port 26.

An extraction port 24 is connected to the collection chamber 14. Flow of gas through the extraction port 24 is governed by a control valve 27. As will be later explained, the extraction port 24 enables some of the contents of the collection chamber 14 to be drawn into a test sample vial 25 for calibration purposes and/or specialty testing circumstances.

Initially, the first, second and third valves 16, 18, and 28 of the collection system 10 are closed. To operate the collection system 10, the first, second and third valves 16, 18, 28 are opened. The flow rate enabled by the first valve 16 is set to be greater than the combined flow rates through the second and third valves 18, 28. This ensures that gas will flow into the collection chamber 14 from the hydrogen source and that no contamination can backflow into the collection chamber 14 from the surrounding environment. The gas is permitted to flow into, through, and out of the collection chamber 14 for a period of time sufficient to purge the collection chamber 14 and the hydrogen separator 20.

After an appropriate purging period, the third valve 28 is closed. This causes hydrogen gas to fill the collection chamber 14 and begin permeating through the hydrogen permeable membrane 22 in hydrogen separator 20. Once the previously mentioned volume of hydrogen gas passes into the collection chamber 24, the first valve 16 is closed and a sample of hydrogen gas is isolated within the collection chamber 14.

The hydrogen separator 20 is brought to an elevated operating temperature of over 450 degrees Celsius. The hydrogen separator 20 contains the hydrogen permeable membrane 22. However, the area of the hydrogen permeable membrane 22 can be made very small and the structure of the hydrogen permeable membrane 22 can be made very robust because it is only exposed to the limited amount of hydrogen gas that is present in the collection chamber 14. In the prior art there are many designs for hydrogen separators. Many such hydrogen separators can be adapted for use by the present invention. However, the non-coil hydrogen separators commercially available from Power+Energy, Inc., of Ivyland, Pa. are preferred. Once the hydrogen gas sample is exposed to the hydrogen separator 20, the hydrogen molecules contained within the hydrogen gas sample begin to pass through the hydrogen permeable membrane 22 within the hydrogen separator 20. The hydrogen atoms that pass through the hydrogen permeable membrane 22 recombine into molecular hydrogen on the surface of the hydrogen permeable membrane 22 that is exposed to free oxygen. The oxygen in the air instantly reacts with the hydrogen molecules to form water. The reaction of the hydrogen molecules with oxygen in the air effectively creates a hydrogen pump that draws molecular hydrogen away from the surface of the hydrogen permeable membrane 22. Dampening valves 31, 33 may be used to limit the flow of air that is exposed to the hydrogen permeable membrane 22. This prevents the hydrogen permeable membrane 22 from overheating outside a safe operating temperature range.

As hydrogen passes through the hydrogen permeable membrane 22 and is drawn away, the pressure of the hydrogen gas sample remaining in the collection chamber 14 decreases. Although the pressure within the collection chamber 14 drops below ambient pressure, hydrogen still passes through the hydrogen permeable membrane 22 due to the fact that the partial pressure of hydrogen gas inside the collection chamber 14 is still much greater then the partial pressure of hydrogen gas in ambient air. Furthermore, as molecular hydrogen forms on the surface of the hydrogen permeable membrane 22, it is instantly removed by its reaction with oxygen. Accordingly, the pressure of molecular hydrogen on the sample side of the hydrogen permeable membrane 22 remains greater than the pressure of molecular hydrogen on the exposed side of the hydrogen permeable membrane 22. This pressure differential biases the flow of hydrogen across the hydrogen permeable membrane 22 from the sample side of the membrane to the exposed side of the membrane.

The collection chamber 14 is left exposed to the hydrogen separator 20 until the pressure in the collection chamber 14 reaches equilibrium. As has been previously stated, the incoming hydrogen gas sample is preferably reduced in pressure to 760 Torr. An exemplary pressure reduction to 1 millitorr concentrates contaminates by a factor of 760,000 times. Furthermore, the passage of 10,000 cubic centimeters of sample gas into a twenty cubic centimeter collection chamber concentrates contaminants by a factor of another 500 times. The concentration factor therefore equals 760,000×500, which equals a total concentration factor of 350 million. This number can be increased by using a larger starting gas volume, a smaller collection chamber 14 and/or producing a lower pressure within the collection chamber 14.

The hydrogen separator 20 draws only hydrogen gas out of the collection chamber 14. Contaminants are concentrated inside the collection chamber 14. Consequently, although the mass of the contaminants introduced into the collection chamber 14 remains constant, the concentration of contaminants per unit of gas sample increases exponentially with the reduction of hydrogen.

Once the pressure within the collection chamber 14 has fallen to equilibrium, a pressure reading of the collection chamber 14 is taken. A capacitance monometer 30 is coupled to the collection chamber 14. The capacitance monometer 14 measures the pressure of the gas remaining in the collection chamber 14. The volume of the collection chamber 14 is known. Dividing the pressure within the collection chamber 14 by the volume of the collection chamber 14 quantifies the mass the of contaminate gasses that were mixed in with the original collection of 10,000 cubic centimeters of gas. Accordingly, the contaminant level on the scale of parts per million or even parts per billion can readily be determined.

The capacitance monometer 30 is coupled to a computer controller 32, as are the various valves 16, 18, 27, 28, 31. The computer controller 30 controls the valves 16, 18, 27, 28, 31 to purge and run a test cycle. The computer controller 30 then makes the simple calculations needed to provide a reading to a user. The result is a simple low cost collection system 10 that can be used determine the concentration of contaminants in any stored volume of hydrogen gas.

By using the present invention system, accurate measurements can be had for contaminant levels as small as a few parts per billion. However, if the gas being sampled is highly pure, the present invention system 10 can be used to detect contamination as low as a few parts per trillion.

In order to calibrate the system 10 or to detect contamination in the accuracy level of parts per trillion, the system is run in the manner previously described. Once the contaminants have been concentrated in the collection chamber 14, a sample of the contaminated gases is drawn out of the collection chamber using the extraction port and opening control valve 27. The drawn sample is then taken to a mass spectrometer 34 and analyzed. Alternatively, the mass spectrometer 34 can be directly connected to the extraction port 24.

Regardless of how a sample is introduced to the mass spectrometer 34, the sample will contain a large concentration of contaminants, if the contaminants are present. Since the collection system 10 acts to concentrate the contaminants in the sample analyzed by the mass spectrometer 34, it will be understood that even small changes in the levels of contamination can be detected. This enables a person to better track when an ultra pure hydrogen generation system is beginning to fail.

It will be understood that the system and method that has been illustrated and described is merely exemplary and that a person skilled in the art can make many modifications to that embodiment. For instance, the shape of the collection chamber and the position of the various ports and valves are a matter of design choice. All such variations, modifications and alternate embodiments are intended to be included within the scope of the present invention as defined by the claims.

What is claimed is:

1. A method of testing contaminant levels in a first volume of gas containing hydrogen gas and contaminant gases, said method comprising the steps of:

providing a collection chamber having a volumetric capacity that is less than said first volume;

providing a hydrogen separator containing a hydrogen permeable membrane, wherein said hydrogen permeable membrane has a first side exposed to said collection chamber and a second side that is isolated from said collection chamber;

introducing said first volume of gas into said collection chamber, wherein said first volume of gas is exposed to said first side of said hydrogen permeable membrane and said hydrogen gas within said first volume of gas permeates through said hydrogen permeable membrane and out of said collection chamber;

actively drawing hydrogen gas away from said second side of said hydrogen permeable membrane by exposing said second side of said hydrogen permeable membrane to a gas that contains oxygen, wherein hydrogen permeating through said hydrogen permeable membrane reacts with said oxygen and is drawn away from said second side of said hydrogen permeable membrane, therein producing a lower partial pressure of said hydrogen gas in said collection chamber and an increased partial pressure of said contaminant gases within said collection chamber;

measuring pressure within said collection chamber with a capacitance manometer; and providing a computer controller that is connected to said capacitance manometer and calculates a contamination level as a function of pressure measured by said capacitance manometer, wherein said contamination level is indicative of a volume of said contaminant gases present in said first volume of gas.

2. The method according to claim 1, wherein said volumetric capacity of said collection chamber is at least 100 times smaller than said first volume of gas.

3. The method according to claim 1, wherein said volumetric capacity of said collection chamber is at least 500 times smaller than said first volume of gas.

4. A method of measuring contaminate gas levels contained within a source of hydrogen gas, said method comprising the steps of:
   providing a collection chamber having a predetermined volumetric capacity;
   purging said collection chamber with said source of hydrogen gas;
   introducing a predetermined volume of hydrogen gas into said collection chamber that is at least 100 times greater that said volumetric capacity of said collection chamber;
   drawing pure hydrogen gas from said collection chamber through a hydrogen permeable membrane until an equilibrium across said hydrogen permeable membrane is reached, therein concentrating contaminants in said collection chamber;
   measuring pressure within said collection chamber with a capacitance manometer; and
   converting said pressure measured by said capacitance manometer into a contaminant concentration level.

5. The method according to claim 4, wherein said hydrogen permeable membrane has a first side and a second side.

6. The method according to claim 5, wherein said step of drawing pure hydrogen gas from said collection chamber includes exposing said predetermined volume of hydrogen gas to said first side of said hydrogen permeable membrane, wherein some of said hydrogen gas permeates through hydrogen permeable membrane and exits said collection chamber.

7. The method according to claim 6, further including the step of actively drawing hydrogen gas away from said second side of said hydrogen permeable membrane.

8. The method according to claim 7, wherein said step of actively drawing hydrogen gas includes exposing said second side of said hydrogen permeable membrane to a gas that contains oxygen, wherein hydrogen permeating through said hydrogen permeable membrane reacts with said oxygen and is drawn away from said second side of said hydrogen permeable membrane.

9. The method according to claim 4, wherein said volumetric capacity of said collection chamber is at least 100 times smaller than said predetermined volume of hydrogen gas.

10. The method according to claim 9, wherein said volumetric capacity of said collection chamber is at least 500 times smaller than said predetermined volume of hydrogen gas.

11. The method according to claim 4, wherein said step of converting said pressure includes providing a computer controller that is connected to said capacitance manometer and calculates a contamination level as a function of pressure measured by said capacitance manometer, said predetermined volume of gas and said volumetric capacitance of said collection chamber.

12. A method of measuring contaminants mixed within a sample of hydrogen gas, said method comprising the steps of:
   tapping a high pressure source of hydrogen gas to obtain said sample of a first volume;
   reducing said pressure of said sample to approximately one atmosphere;
   introducing said sample into a collection chamber that has a volumetric capacity lower than said first volume;
   drawing pure hydrogen gas out of said collection chamber using a hydrogen separator until pressure within said collection chamber falls to a residual pressure;
   measuring said residual pressure with a capacitance manometer; and
   converting said residual pressure into a contaminant level value.

13. The method according to claim 12, wherein said volumetric capacity of said collection chamber is at least 100 times smaller than said predetermined first volume.

* * * * *